Figure 1:
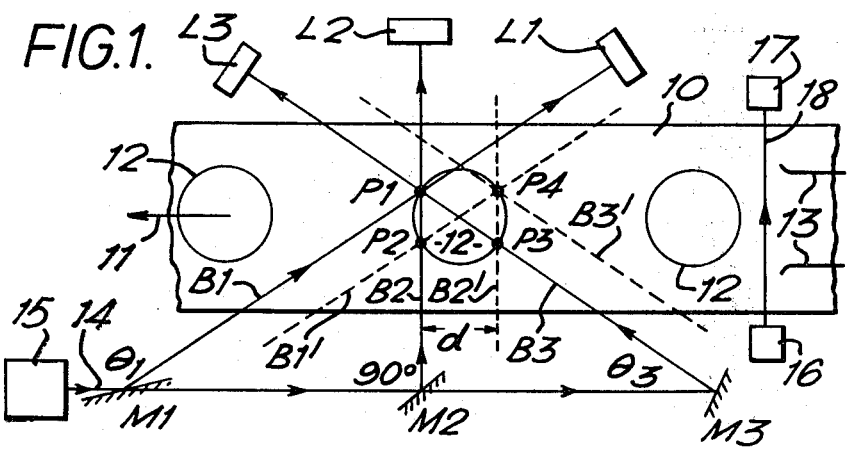

United States Patent [19]

O'Connor et al.

[11] 4,411,522
[45] Oct. 25, 1983

[54] APPARATUS FOR THE INSPECTION OF TRANSLUCENT CONTAINERS

[75] Inventors: Brendan F. O'Connor, Foxrock; John O. Phillips, Ballyvourney; Charles M. Webb, Foxrock, all of Ireland

[73] Assignee: Udaras Na Gaeltachta, Furbo, Ireland

[21] Appl. No.: 248,154

[22] Filed: Mar. 30, 1981

[30] Foreign Application Priority Data

Mar. 28, 1980 [IE] Ireland .................................. 650/80
Aug. 6, 1980 [IE] Ireland .................................. 1636/80
Nov. 4, 1980 [IE] Ireland .................................. 2279/80

[51] Int. Cl.³ .......................................... G01N 21/90
[52] U.S. Cl. .............................. 356/240; 250/223 B
[58] Field of Search ................... 356/240, 427, 428; 250/223 B, 224; 209/524, 525, 526

[56] References Cited

U.S. PATENT DOCUMENTS

| 3,684,385 | 8/1972 | Einfalt et al. ........................ 356/240 |
| 3,932,042 | 1/1976 | Faani et al. .......................... 356/240 |
| 4,140,901 | 2/1979 | Fischer et al. ..................... 356/240 X |
| 4,280,624 | 7/1981 | Ford ............................... 356/240 X |

FOREIGN PATENT DOCUMENTS 2036301  6/1980  United Kingdom ................ 356/427

Primary Examiner—John K. Corbin
Assistant Examiner—Matthew W. Koren
Attorney, Agent, or Firm—Sughrue, Mion, Zinn, Macpeak & Seas

[57] ABSTRACT

The present Specification describes an apparatus for the inspection of translucent containers comprising a conveyor (10) for transporting a container (12) through an inspection zone, and means (15, M1,M1,M3) for directing a plurality of light beams (B1,B2,B3) sideways at the container during its movement through the zone. Each light beam is directed at the side of the container from a different direction relative to the container, and deflection means cause each of the beams to repeatedly scan the side of the container in a vertical direction as the container moves fully through each beam. A respective opto-electronic light collector (L1,L2,L3) is provided for each beam for providing a respective signal S representing the amount of light falling thereon from the respective beam after transmission through the container, and signal processing circuitry (40) is associated with each light collector to examine the signal therefrom according to a predetermined criterion to generate a fault-indicating signal (41) when such criterion is fulfilled. Means are provided for allocating to each beam a respective area of the container sidewall for which any such fault-indicating signal can be regarded as resulting from an actual fault rather than from a characteristic of an acceptable container, and any fault-indicating signal generated when the respective beam is not scanning the allocated area of the container sidewall is suppressed.

In one embodiment the scanned area of the sidewall of the container allocated to each beam is a rectangle defined by the duration of a gating signal and the scan height of the beams.

In a second embodiment, however, the allocated area of each beam is defined by a random access memory (42) having stored therein binary information identifying those regions of an acceptable container from which fault-indicating signals may be generated according to the said criterion even in the absence of a fault.

11 Claims, 7 Drawing Figures

(a)

(b)

(c)

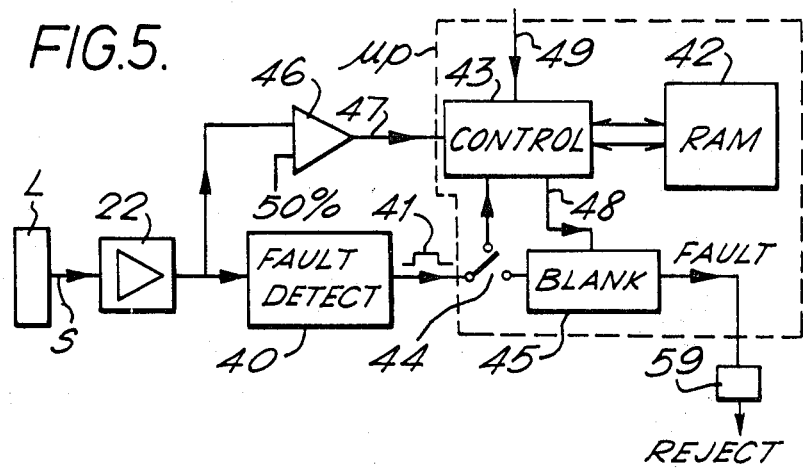
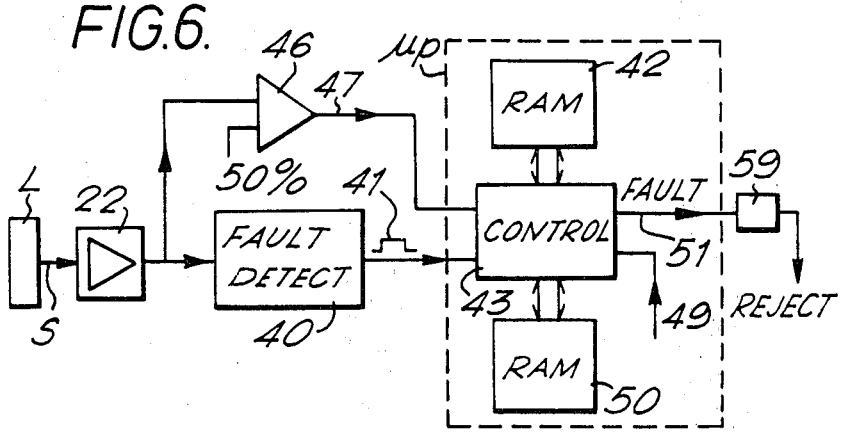
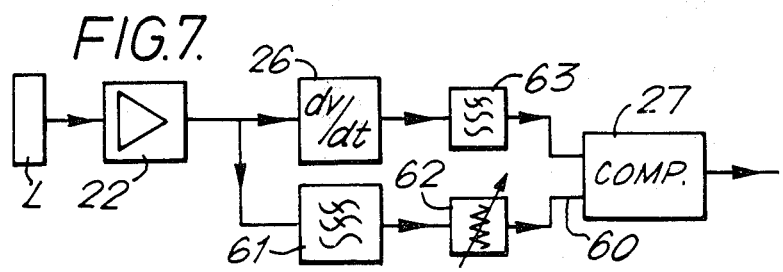

APPARATUS FOR THE INSPECTION OF TRANSLUCENT CONTAINERS

This invention relates to an apparatus for the inspection of translucent containers, such as glass bottles, for faults.

Bottle inspection systems are known wherein a rotating bottle is scanned by a single vertically scanning beam passing completely through the bottle from one side to the other and intersecting the vertical axis of the bottle.

While a very high resolution can be obtained from such systems, situations can be envisaged where the requirement for resolution is less high, and consequently the economic justification for an expensive system is lacking, or where the containers are not handleable in the manner required by these systems due to their physical condition, such as heat.

The fact that the beam goes completely through the container can be used to detect occlusions on the front or back of the container as seen by the scanning beam, and it is therefore an object of the invention to provide an inspection apparatus which may be constructed more cheaply than those heretofore mentioned.

Accordingly, the present invention provides an apparatus for the inspection of translucent containers comprising means for transporting a container through an inspection zone, means for directing a plurality of light beams sideways at the container during its movement through the zone, each light beam being directed at the side of the container from a different direction relative to the container, deflection means for causing each of the beams to repeatedly scan the side of the container in a direction transverse to the direction of motion of the container as the container moves fully through each beam, a respective opto-electronic light collector for each beam for providing a signal representing the amount of light falling thereon from the respective beam after transmission through the container, signal processing circuitry associated with each light collector and adapted to examine the signal therefrom according to a predetermined criterion to generate a fault-indicating signal when such criterion is fulfilled, means allocating to each beam a respective area of the container sidewall for which any such fault-indicating signal can be regarded as resulting from an actual fault rather than from a characteristic of an acceptable container, and means for suppressing any fault-indicating signal generated when the respective beam is not scanning the allocated area of the container sidewall.

In one embodiment the scanned area of the sidewall of the container allocated to each beam is a rectangle defined by the duration of a gating signal and the scan height of the beams. However, this is a somewhat inflexible arrangement in that it can only efficiently cope with one size of bottle. If a different diameter and/or height bottle is to be inspected, the duration of the gating signal and/or the scan height would have to be changed. Furthermore, the arrangement is only really suitable for generally straightsided bottles, since for bottles with undulating sides the duration of the gating signal would have to be determined by the minimum diameter so that portions of greater diameter would remain unscanned. For the same reason, the above arrangement does not inspect the neck area of the bottle, nor the shoulder between the neck and main body portion.

Preferably therefore, the means defining the allocated area of each beam comprises a respective random access memory (RAM) having stored therein binary information identifying those regions (referred to herein as fault-invalid regions) of an acceptable container, as viewed in the direction of the beam, from which fault-indicating signals may be generated according to the said criterion, and the suppression means is responsive to the stored binary information to supress any fault-indicating signal generated while scanning a fault invalid region of the container.

In such case the contents of the RAM are preferably the cumulative results of previously scanning a large number of containers (for example 50) which have been determined to be acceptable by other means (for example by manual inspection and measurement), and storing each fault-indicating signal so generated as a significant bit (1 or 0) in the RAM, the bit cells of the RAM being addressed for each container in the same predetermined sequence in synchronism with the scanning so that each fault-indicating signal is stored at a bit cell location corresponding to the current position of the beam relative to the container. The number of containers previously scanned in this way and contributing to the cumulative result in the RAM sets the degree of tolerance afforded by the system.

Using the RAM, the suppression of the fault-indicating signals may take various forms. In one example this is achieved by reading out the contents of the RAM in the said predetermined sequence in synchronism with the scanning of the container, and blanking any fault-indicating signal which occurs simultaneously with an output of the RAM which identifies the point currently being scanned by the beam as lying within a fault-invalid region of the container. Alternatively, the suppression can be achieved by storing the fault-indicating signls generated during the scanning in a further RAM (which may be an unused part of the first RAM) in the said predetermined sequence, subsequently reading out and comparing the contents of the first and further RAMs in the same sequence, and blanking any fault-indicating signal which occurs as output from the further RAM when the corresponding output from the first RAM indicates a fault-invalid region of the container. In either case, however, the read-out of the first RAM should of course be non-destructive.

The criterion used in the invention by the signal processing circuitry for detecting faults may be of any desired kind. Thus the signal processing circuit may operate by comparing the sum signal from the light collector with a threshold level in an automatic threshold tracking circuit (ATTC) as in the case of the arrangement disclosed in our prior Irish Patent Application No. 320/79 (PROBECON I). An ATTC circuit is a comparison circuit wherein the threshold level against which the sum signal is compared is derived from the sum signal itself so as to accommodate containers whose wall thickness and/or colour density may vary significantly. The threshold signal is effectively a smoothed version of the sum signal which lags the latter and is offset from it by a predetermined amount.

Alternatively, the signal processing circuitry associated with each light collector may be adapted to differentiate the signal therefrom so as to provide a further signal representing the rate of change of amplitude of the light collector signal, and to compare the further signal with a reference threshold level so as to generate a fault-indicating signal when the rate of change of amplitude exceeds the threshold level.

In the simplest case the signal processing circuitry may simply compare the sum signal with a fixed threshold, or with a threshold which is a predetermined function of the vertical position of the beam, as described in U.K. Patent Specification No. 1,430,547.

Whatever criterion is chosen, when a RAM is used to define the allocated areas it is generally necessary for the same criterion to be used both in generating the initial accumulated information in the RAM and for the subsequent testing of containers. An exception to this, however, is where the criterion used for testing is less sensitive than the criterion used for the initial accumulation of information, i.e. it cannot generate a fault-indicating signal from an acceptable container outside the fault-invalid regions defined by the RAM. A particularly advantageous arrangement, when the same differentiating and threshold comparison circuit is used both to generate the contents of the RAM and to subsequently inspect the container, is to set the reference threshold for the first operation (accumulation of RAM contents) at a lower level than that used in the subsequent inspection. This enables one to accommodate acceptable undulations in the internal surface of the container which in conventional bottle manufacture tend to be greater than those in the external surface and thus may fall outside the tolerance established by the RAM despite passing a large number of acceptable containers through the system. Furthermore, a fault-detecting circuit set to detect occulsive faults by comparison with a fixed threshold can be used in conjunction with a RAM whose contents were accumulated by an ATTC circuit or differentiation, provided that the fixed threshold level is chosen to represent a level of opacity greater than that occurring anywhere outside the fault-invalid regions defined by the RAM. Indeed, a fixed threshold is most efficient in detecting regions of "smoke" in the glass, which might not be reliably detected by an ATTC circuit or by differentiation since it does not have well-defined edges, and therefore it may be desirable to use a fixed threshold fault-detecting circuit in addition to an ATTC or differentiating circuit when testing.

A fault-indicating signal generated outside a fault-invalid region defined by the RAM may be assumed to represent an actual fault in the container. However, it would generally not be desirable to reject a container on the basis of only a single or a very few valid fault-indicating signals since these may arise from noise in the electrical components of the system, or from only small but acceptable faults or variations from the tolerance established by the contents of the RAM. Therefore, it is preferable for each container to sum the number of valid fault-indicating signals in respect to each light collector and only reject when the total in respect of any one light collector exceeds a predetermined limit. Alternatively, one may sum the overall number of valid fault-indicating signals from all light collectors and reject when the overall total exceeds a certain limit. The approach chosen will depend upon the number of light beams used, the sensitivity required, the characteristics of the containers being scanned, and the precise nature of the signal processing circuitry used. This summing procedure may also be adopted in the embodiments where a RAM is not used, to reduce the incidence of false rejects.

The different areas scanned by the beams may be scanned simultaneously, in which case the beams will be directed towards a substantially common position through which the container passes, or the different areas may be scanned successively in which case the beams will be directed at successive positions along the inspection zone.

Preferably three light beams are used, one being directed at the side of the container at an angle normal to the direction of motion of the container, and the other two beams being directed at the side of the container at an acute angle and an obtuse angle respectively, taking the forward direction of the container as the 0° axis. In this case, using three beams, it is generally preferable to sum the number of valid fault-indicating signals individually in respect to each light collector, and reject when the total in respect of any one collector exceeds a certain limit. On the other hand, it is possible to use only two beams, in which case it is generally preferable to sum the total number of valid fault-indicating signals from both light collectors and only reject when the overall total exceeds a certain limit.

Figure 2:
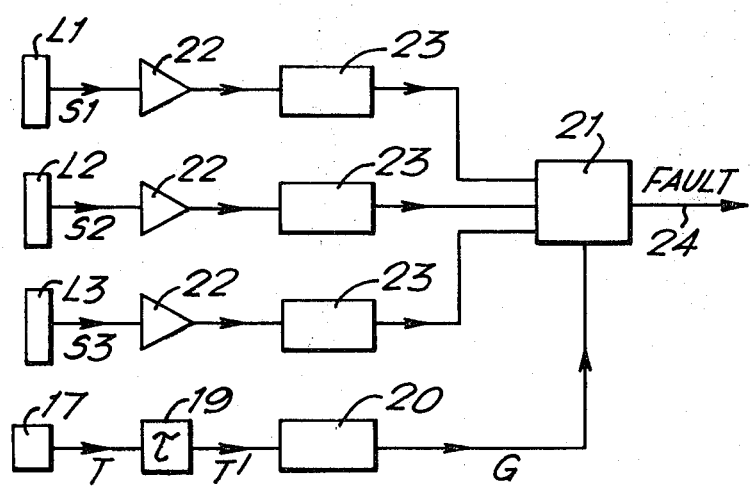
Figure 3:
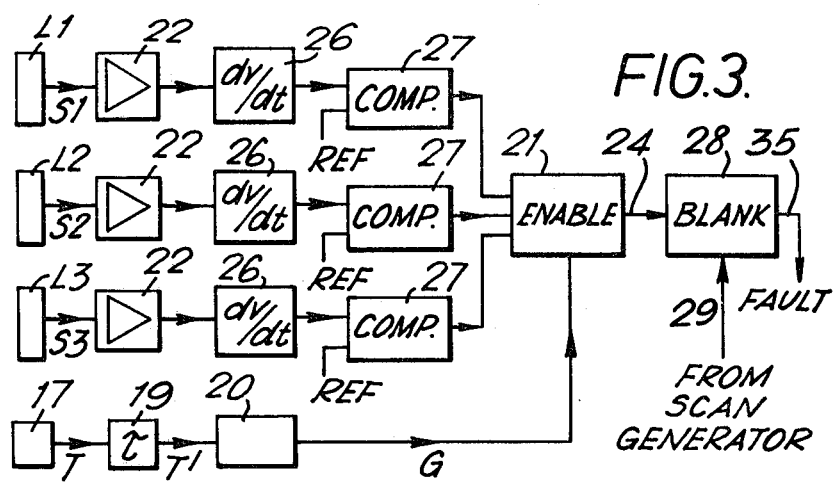
Figure 4:
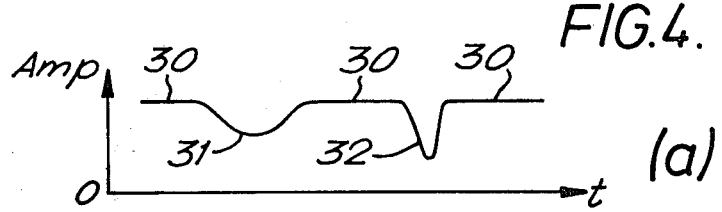
Figure 4:
Figure 4:
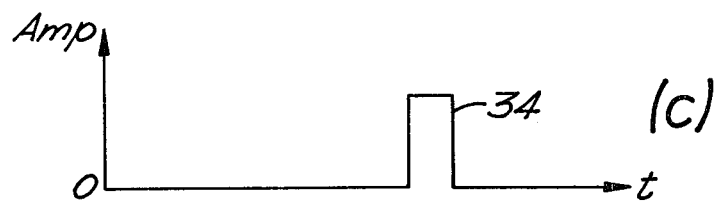

Embodiments of the invention will now be described, by way of example, with reference to the accompanying drawings, wherein:

FIG. 1 is a schematic top plan view of an apparatus for inspecting bottles for occlusive and refractive faults, FIG. 2 is a block circuit diagram of a first embodiment of electricl signal processing circuitry associated with the apparatus of FIG. 1, FIG. 3 is a block circuit diagram of a second embodiment of signal processing circuitry which may be associated with the apparatus of FIG. 1, FIG. 4 shows simplified signal waveforms illustrating the principle of operation of FIG. 3, FIG. 5 is a block circuit diagram of a third embodiment of signal processing circuitry which may be associated with the apparatus of FIG. 1, FIG. 6 illustrates a modification of the circuitry of FIG. 5, and FIG. 7 is a block schematic diagram of a preferred form of fault detection circuit operating by differentiation of the sum signal and subsequent comparison with a threshold which varies as a function of the transmission of the container.

Referring now to FIG. 1, the inspection apparatus comprises an endless conveyor 10 driven with continuous motion in the direction indicated by arrow 11. It is to be understood that the apparatus is shown in plan view, so that the conveyor 10 moves in a horizontal plane. Bottles 12 to be inspected are separated and fed onto the conveyor 10 from a conventional bottle screw (not shown) and are located centrally on the conveyor 10 by guides 13 at the output of the screw. This ensures that the bottles 13 are located in the correct position for subsequent inspection. In FIG. 1, the bottles as assumed to have main body portions of substantially circular cross-section as shown. This first embodiment of the invention is not intended to examine the neck portion of the bottles which are therefore not shown in the figure.

After leaving the guides 13 each bottle approaches an inspection zone wherein three intersecting spot-form light beams B1, B2 and B3 are directed sideways at the bottle. The three beams B1, B2 and B3 are derived from an initial single beam 14 by semi-reflective mirrors M1, M2 and M3 respectively. The mirrors cause the three beams to strike the side of the bottle at different angles relative to the direction of motion of the conveyor 10.

Thus beam B1 makes an obtuse angle $\theta_1$ with the direction of motion of the conveyor 10, beam B2 is directed normal to the direction of motion of the conveyor, and beam B3 makes an acute angle $\theta_3$ to the direction of motion of the conveyor, the forward direction of the conveyor being taken as the 0° axis.

The initial single beam 14 is generated by a scan generator 15 which not only generates the beam 14 but also causes to repeatedly scan in the vertical direction, i.e. the direction normal to the plane of FIG. 1. The amplitude of the vertical scan is determined by the height of bottle to be examined since the vertical scanning is of course reproduced in each of the beams B1 to B3. Although not shown in FIG. 1, means are preferably provided to equalize the path lengths of each of the beams B1 to B3 from the generator 15 to the bottle, so that each beam has the same scan amplitude at the bottle. The scan generator 15 may be of a type using a rotating polygonal mirror and will not be further described here. The beam 14 is preferably a laser beam.

Each beam B1, B2 and B3 falls upon a respective light collector L1, L2 and L3. The light collectors may each be constructed as a matrix of photo-diodes disposed behind a diffusing screen and separated one from another by a grid of thin-walled boxes. Such a construction of light collector is described in our copending Irish Patent Application No. 320/79. However, whereas in that previous Application the outputs of the diodes were examined selectively to search for certain non-occlusive faults, in the present embodiment the diode outputs of each light collector are merely summed so as to provide a respective electrical signal S1, S2 and S3 (FIG. 2) representing the total amount of light falling on the collector from the respective beam.

The apparatus further includes a light emitter 16 and a receiver 17 disposed on opposite sides of the conveyor 10. The receiver 17 generates a signal T (FIG. 2) when the beam of light 18 between the emitter and receiver is interrupted by the forward edge of a bottle 12 emerging from the guides 13.

The operation of the above-described apparatus will now be given, referring also to FIG. 2 which is a block diagram of the circuitry associated with the light collectors L1 to L3 and receiver 17.

During operation, bottles 12 are fed one by one on to the conveyor 10 and are transported with continuous motion and without rotation through the inspection zone. As the forward edge of a bottle 12 interrupts the beam 18, the signal T is generated as previously described and this signal T is passed through a delay circuit 19 (FIG. 2) to a timing circuit 20. The delay imposed by the circuit 19 is chosen in relation to the speed of the conveyor 10 such that the delayed signal T¹ appears at the output of 19 precisely at the moment when the bottle 12 arrives at the position shown for the centre one of the three bottles shown in FIG. 1; i.e. when the edge of the bottle meets the point of intersection of the three beams B1, B2 and B3. This point on the bottle 12 is labelled P1.

Upon the appearance of the delayed signal T¹, the timing circuit 20 provides a gating signal G which persists for sufficient time for the bottle to move through a distance d whereupon the point of intersection of the three beams is now at P4. It is to be understood that for simplicity the movement of the bottle 12 through distance d has not been shown in FIG. 1; instead the positions of the three beams B1, B2 and B3 relative to the bottle have been shown at B1¹, B2¹ and B3¹ respectively after the movement of the bottle through the distance d. When the intersection of the three beams B1 to B3 reaches point P4 the gating signal G ceases.

It will be seen by inspection of FIG. 1 that during the motion of the bottle through the distance d the beam B1 scans the area of the bottle between P1 and P2, the beam B2 scans the area between P2 and P3, and the beam B3 scans the area between P3 and P4. Thus, since P1 and P4 are separated (via P2 and P3) by more than 180° around the circumference of the bottle, and since each beam passes completely through the bottle, the entire sidewall of the bottle is scanned during the movement through the distance d, insofar as the sidewall lies within the scan amplitude of the beams.

The reason for using three scanning beams instead of a signal scanning beam is that if a single beam, for example beam B2, were used, the excessive thickness of glass through which the beam would have to travel when first encountering (and finally leaving) the edge of the bottle tangentially would deflect the beam away from the associated light collector L2 and/or obscure the beam to such an extent, that reliable fault detection could not be achieved across the whole width of the bottle. Thus the point P1 is chosen so that the beam B2 is already sufficiently inside the forward edge of bottle 12 that it will fall on its light collector L2 in the absence of serious occlusive or refractive faults. The point P2 is similarly chosen in relation to the rear edge of the bottle.

The purpose of the gating signal G is to ensure that the results of the bottle inspection as determined by the circuit of FIG. 2 are only passed on when the beam B2 is scanning the area between P2 and P3. To this end the signal G is passed to a gating circuit 21 which is normally closed but is opened by the signal G. Thus although the beams B1, B2 and B3 are continuously scanning, both in the presence and absence of a bottle in the inspection zone, only the results of the scanning which occur during the inspection of the area between P2 and P3 are passed on.

Since for the reasons mentioned above a single beam B2 cannot scan the entire sidewall of the bottle, the two further beams B1 and B3 are provided. While B2 is scanning P2 to P3 the beam B1 is simultaneously scanning P1 to P2 and the beam B3 is simultaneously scanning P3 to P4. The angles $\theta$, and $\theta_3$ of the beams B1 and B3 are chosen so that, as in the case of beams B2, at the beginning and end of the period determined by the duration of the gating signal G and corresponding to the movement of the bottle 12 through the distance d, these two further beams are also sufficiently inside the bottle that they do not have to pass through an excessive thickness of glass.

In the circuit of FIG. 2, the signals S1, S2 and S3 from the light collectors are amplified in respective preamplifiers 22 to ensure that the signals have a sufficiently large amplitude to enable them to be processed in a subsequent automatic tracking threshold circuit (ATTC) 23 previously referred to and described in our copending Irish Patent Application No. 320/79. In the ATTC circuit 23 the signal is compared with a reference threshold level, and when the signal falls below the reference level a provisional fault-indicating signal R is generated at the output of the circuit 23. The signal R is provisional because it is only during the existence of the signal G that any such signals are relevant, for the reasons discussed above, and appear as valid fault-indicating signals at the output 24 of the gating circuit 21. Any of the three beams B1, B2 and B3 can generate a signal at 24, and such signal can either activate an alarm signifying that the appropriate bottle is faulty, or more preferably actuate a reject mechanism of known kind, preferably only after a predetermined number of such signals have been counted in respect of any one container. In the case of non-clear glass bottles, it is further desirable to insert a known automatic signal amplitude equalisation (ASAE) circuit (not shown) before each ATTC circuit 23, such ASAE circuit being described in U.K. Patent Specification No. 1 430 547.

It is to be understood that in the bottle inspection it is possible for the three areas defined by P1 to P2, P2 to P3, and P3 to P4 to be scanned at successive positions along the conveyor rather than simultaneously as described. However, this would require individual delay elements 19, timing circuits 20, and gating circuits 21 for each beam, thus increasing the cost. Furthermore, the three different areas effectively scanned by the beams may overlap if desired, rather than precisely abut as shown. This would allow some relaxation in the precision of the apparatus. Finally, if the entire scanning arrangement is repeated further down the line, by an additional series of mirrors, the same beam 14 can be taken to the other side of the containers 12 and direct scanning of the entire container can then be accomplished. However, for the sort of resolution desired by the present embodiment the "through the container" scanning will be just as effective.

The particular applications for the apparatus described above will either be in the "hot end" area of a container manufacturing plant or in the "cold end" of the smaller glassworks where overall inspection of the container to a high degree of sophistication is not possible for economic reasons.

In the above embodiment of the invention the signal processing circuitry effectively compares each light collector signal with a reference threshold level to generate a fault-indicating signal when the collector signal falls below the threshold, it being assumed that this latter condition represents an occlusive or severe refractive fault indicative of a defective bottle.

However, this apparatus is most effective for relatively plain bottles only, since heavy embossing, lettering or other ornamentation can cause the light collector signal to fall substantially so these features cannot reliably be distinguished from a true defect by a simple comparison of the light collector signal with a threshold level, particularly when it is desired to detect relatively small faults.

A second embodiment of the invention will therefore now be described with reference to FIGS. 3 and 4 which can provide better discrimination between true defects and heavy embossing, lettering or decorative ornamentation. This second embodiment is based upon the realisation that although heavy embossing and the like may cause a significant drop in signal amplitude comparable with that produced by certain defects, the rate of change of amplitude in such cases is generally relatively small, whereas the rate of change in signal amplitude for a defect such as an occlusion or severe refractive fault is generally much higher. Thus differentiation provides the key to discriminating between these features.

The signal from the light collector may be differentiated by applying the signal to an analog delay line and applying the signal levels at two adjacent tapping points on the delay line to a difference amplifier. While this is not true differentiation it is a close approximation which will provide, for present purposes, an adequate discrimination between slow and rapid changes in amplitude level, and the term "differentiate" is to be interpreted accordingly to include circuits producing such discrimination.

It is to be understood that the scanning apparatus used in performing the second embodiment may be substantially the same as that described with reference to FIG. 1 above and thus the details thereof will not be repeated here. However, it is necessary to note that each light collector should be of sufficiently large dimensions as to collect substantially all of the light from its associated laser beam after passage through an acceptable bottle, taking into account the acceptable and expected dispersion and refraction of the light by the bottle due to embossing the like.

Much of the signal processing circuitry may also be the same as in the first embodiment, and in FIG. 3 of the present embodiment those components which serve the same function as equivalent components in FIG. 2 of the first embodiment have been given the same reference characters. The differences, however, are the replacement of the ATTC circuits 23 of the prior embodiment in each case by the combination of a differentiating circuit 26 and a comparison circuit 27 in series between the pre-amplifier 22 and the enable gate 21, and the addition of a blanking gate 28, whose purpose will be described later, at the output of the enable gate 21.

As in the previous embodiment, each sum signal $S_1$, $S_2$ and $S_3$ is preamplified in a respective pre-amplifier 22. FIG. 4a represents part of a typical pre-amplified signal in highly simplified form for purposes of illustration only. The average level of the signal S is represented by the components 30 of the signal, the drop in amplitude produced by a region of embossing or the like is represented by the component 31, and the drop in amplitude produced by an occlusion or severe refractive defect is represented by the component 32. It will be seen that although the drop in amplitude is comparable in respect of each signal component 31 and 32, the rate of change of amplitude of the component 31 resulting from the embossing is much less than that of the component 32 resulting from the defect.

This difference is enhanced by the differentiating circuit 26, of which the corresponding signal output is shown at FIG. 4b. It will be seen that the signal component $31^1$, corresponding to the component 31 of FIG. 4a, is much smaller in amplitude than the component $32^1$ corresponding to component 32 in FIG. 4a.

By setting a suitable reference threshold level on the comparison circuit 27, it is possible for the latter to distinguish between the signal components $31^1$ and $32^1$, and thereby between the embossing and the true defect. The reference level, shown at 33 in FIG. 4b, is set so that the rates of change of signal amplitude to be expected from an acceptable bottle do not produce a differentiated signal component which falls below this level, whereas abrupt changes of amplitude caused by occlusions or severe refractive faults provide a differentiated signal which does fall below this level. When this latter condition occurs, a pulse-form fault-indicating signal is generated by the comparison circuit 27, as shown at 34 in FIG. 4c.

As in the previous embodiment, this fault-indicating signal is only provisional at this stage, and can only pass further during the occurrence of the enable gating signal G, i.e. when the beam is sufficiently inside the bottle to avoid the effect of excessive glass thickness in the path of the beam at the leading and trailing edges of the bottle. Also, because the vertical jump of the scanning beams from the end of one vertical scan to the beginning of the next may cause an abrupt change of signal amplitude leading to a false signal, it is necessary to blank the output 24 of the enable gate 21 during the retrace or flyback period of the beams. This is achieved by applying a momentary blanking signal on a line 29 to the blanking gate 28 each time that the beams retrace. This blanking signal on line 29 may be derived from the scan generator. Only when a signal such as that shown in FIG. 2c passes both gates 21 and 28 does it appear as a valid fault-indicating signal at the output 35.

In the two embodiments described above, since fault-indicating signals may arise from the intersection of the light beam by the edges of the bottle, or from the excessive glass thickness traversed by the beam at the edges of the bottle, each beam is allocated a respective area, well inside the periphery of the bottle as viewed by the beam, and any fault-indicating signal arising from scanning outside this area is suppressed. The area allocated to each beam is, in the embodiments described, defined by the height of the vertical scan of the beam and the duration of a gating signal, i.e. it is a rectangle.

For the reasons set out previously this is a somewhat inflexible arrangement and a third embodiment of the invention will now be described with reference to FIGS. 5 and 6 which uses a random access memory matrix (RAM) to define the area allocated to each beam.

Once again it is to be understood that the scanning apparatus used in performing this third embodiment may be substantially the same as that described with reference to FIG. 1 above, and that each light collector should be of sufficiently large dimensions as to collect substantially all of the light from its associated laser beam after passage through an acceptible bottle, taking into account the acceptable and expected dispersion and refraction of the light by the bottle due to embossing and the like. However, the vertical scan height may be increased to include the neck and shoulder area of the bottle. Furthermore, the elements 16 to 18 of the prior embodiments are not required in the present case.

The difference between this and the two embodiments described above lies in the signal processing circuitry. The signal processing circuitry used in the present embodiment is shown in FIG. 5 for one of the light collectors L, although it is to be understood that a similar but independently operating circuit is respectively associated with each of the three light collectors.

As in the previous embodiments, the sum signal S is amplified in a preamplifier 22 to provide a suitable level of signal for further processing. Next the amplified sum signal is passed to a fault-detection circuit 40, which can operate according to any desired criterion to detect faults, an hereinbefore discussed. Whatever form of fault detection is used, however, it involves a comparison of a signal derived from the light collector with a reference threshold level, and the circuit 40 is adapted to generate a pulse-form fault-indicating signal 41 for so long as the threshold is exceeded.

Since the vertical scanning in the inspection zone is performed continuously, as each container passes fully through the zone it will be appreciated that the circuit 40 will generate fault-indicating signals not only in respect of actual faults, but also in regions at and adjacent the periphery of the container (as viewed in the direction of the beam) even when such container is acceptable. For example, a fault-detecting circuit operating by differentiation will provide a fault-indicating signal each time the beam intersects the shoulder of the container. It is therefore necessary to suppress those fault-indicating signals which are generated as a result of scanning a characteristic of an acceptable container. This is achieved by the use of a random access memory matrix 42 comprising rows and columns of bit cells, and which contains binary information identifying those regions (referred to herein as fault-invalid regions) of an acceptable container, as viewed in the direction of the beam, from which fault-indicating signals may be generated according to the criterion used by the circuit 40 even through no actual fault is present.

Before describing the testing of containers using the RAM 42, the method by which the binary information is stored in the RAM will first be described. This storage of binary information is performed during what may be called the "learning mode" of the system.

In the learning mode, the output of the circuit 40 is passed to a control circuit 43 for the RAM 42 via a switch 44, and the beam is set for continuous vertical scanning. Now a succession of containers which have been determined by other means to be acceptable are passed through the inspection zone on the conveyor. The leading edge of each container is detected by a comparison circuit 46 which compared the amplified sum signal from 22 with a threshold level set at 50% of the maximum signal (corresponding to no intervening container), and supplies a "start" signal on line 47 to control circuit 43 when the sum signal drops below this level.

Upon receipt of the start signal, the control circuit 43 addresses or scans down consecutive columns of the RAM 42 in synchronism with the vertical scans of the beam, starting with the next vertical scan after the receipt of the start signal, each column of the memory being allocated to a respective vertical scan of the beam. To achieve synchronism of column addressing with the vertical scanning of the beam the control circuit has an input 49 which receives a signal at the beginning of each vertical scan from the scan generator. During the scanning of each column of the memory, a binary 1 is set in the bit cell of the memory currently being addressed when a pulse-form signal 41 is present at the output of the circuit 40. This is repeated for each vertical scan of the container until the control circuit 43 determines that the trailing edge of the container has left the beam, as indicated for example by the continuous absence of a signal on line 47 for a complete vertical scan.

The result, after a single container has passed through the inspection zone with the system in the learning mode, is a pattern of binary 1's in the memory 42 which corresponds to the pattern of fault-indicating signals generated by the acceptable container. This is repeated for a large number of acceptable containers (for example 50) with a cumulative addition of binary 1 bits in the memory 42 i.e. a binary 1 is inserted in a bit cell where one is not present from scanning a previous container, but previously inserted binary 1's remain. The final result therefore is a pattern of binary 0 bits in the memory 42 which defines that area of the container sidewall for which any fault-indicating signal can be regarded as resulting from an actual fault, and a complementary pattern of binary 1 bits identifying the fault-invalid regions of the container sidewalls.

When a sufficient number of acceptable containers have been passed through the system in the learning mode to provide a sufficient spread of binary 1 bits in the memory to accommodate all containers which could be regarded as acceptable, the learning phase is complete and the testing of containers can begin.

This is achieved by switching the output of the circuit 40 to a blanking circuit 45 via the switch 44, and passing the containers one by one through the inspection zone. In this "test mode" the scanning or addressing of the memory 42 is again triggered for each container by a start signal from circuit 46 on line 47 and proceeds column by column in synchronism with the vertical scanning of the beam, but this time the contents of the memory are non-destructively read out. Each time that a binary 1 is received by the control circuit 43 from the memory, the control circuit provides a blanking signal on line 48 to the blanking circuit 45. This ensures that any fault-indicating signal 41 which appears at the output of the circuit 40 is suppressed if it occurs while the beam is scanning a fault-invalid region of the container. Thus those fault-indicating signals which do pass the blanking circuit 45 may be regarded as representing actual faults in the container.

These valid fault-indicating signals are counted in a counter 59 either together with any similar signals received from the processing circuitry associated with the other two light collectors or individually in respect of each light collector to provide a container reject signal when for any container the total of valid fault-indicating signals in respect of any one light collector, or alternatively the overall total in respect of all three light collectors, exceeds a certain limit, as discussed earlier. In the latter case it is to be understood that the counter 59 is common to all three signal processing circuits, and has inputs (not shown) from the two circuits not shown in FIG. 5.

An alternative technique for suppressing the invalid fault-indicating signals (i.e. those signals which are generated while the beam is scanning a fault-invalid region of the container) is shown in FIG. 6. In this case in the test mode the fault-indicating signals are stored in a second RAM 50 (which may be an unused part of the first RAM 42), the second RAM 50 being addressed column by column in synchronism with the vertical scanning in precisely the same way as the RAM 42 was addressed during the learning mode. Thus at the end of scanning a container the RAM 50 contains a pattern of binary 1 bits corresponding to the fault-indicating signals generated by that container. Now the control circuit 49 reads out and compares the contents of the two RAMs 42 and 50 in the same sequence, and blanks any fault-indicating signal which occurs as output from the RAM 50 when the corresponding output from the RAM 42 is a binary 1. Any fault-indicating signal read out from RAM 50 which is not blanked is outputted on line 51 and may be taken to represent an actual fault.

In a practical example of this third embodiment, the diameter of each spot beam of light is 1 mm at the container, and each beam makes several hundred vertical scans across the full width of a container 60 mm in diameter, thereby providing a considerable degree of overlap of consecutive scans. The information in RAM 42 thus occupies several hundred columns. Furthermore, each vertical column of the memory is clocked at a rate corresponding to about 60 bit cells per vertical scan, so that one bit cell represents an element of length of about 1/60th of the vertical scan height of the beam.

Furthermore, the elements contained within the dotted rectangles in FIGS. 5 and 6 and the functions performed thereby as described above, may be embodied in a suitably programmed commercially available microprocessor, using the control circuit and random access memory of the microprocessor. Where the width of the container is so great that, for the chosen conveyor speed, the number of vertical scans required to cover the full width of the container is greater than the storage capacity of the RAM 42 (typically 600 columns), it is clearly possible to arrange for the control circuit 43 to ignore the results of every $n^{th}$ scan both in the learning and test modes, where n is chosen to bring the number of scans actually used within the capacity of the RAM.

The advantage of the present embodiment is that the system can be readily adapted to accommodate different shaped bottles or containers merely by providing a new set of binary information in the RAM 42 in the learning mode, and that the area available for valid inspection by each beam is greater than in the previous embodiments particularly for bottles of nonconstant cross-section, so that substantially the entire surface of the container is scanned for faults, including the neck and shoulder areas.

An advantageous form of the differentiating and threshold comparison circuit for fault detection is shown in FIG. 7. In FIG. 7, the amplified sum signal is differentiated as before in a differentiating circuit 26 and compared in a comparison circuit 27 with a reference threshold level applied at 60. However, in this case the threshold level is derived from the amplified sum signal via a low pass filter 61, so that variations in the thickness or colour density of the glass can be accommodated. The threshold reference level is thus a function of the average transmission of the container at the point concerned, the low pass filter 61 serving to filter out rapid fluctuations in the transmission due to faults or acceptable characteristics of the container. The actual level of the threshold, as a percentage of the average transmitted signal, is set by a potentiometer 62. This form of differentiating and comparison circuit may be used in the embodiment of FIGS. 3 and 4 or in the embodiment of FIGS. 5 and 6. The advantage of this arrangement is that a higher detection of faults is achieved, since the denser the bottle or container the more sensitive the comparison circuit must be to detect a given fault, since for a dense bottle (due to thicker glass or a deeper colouration) a given fault will give a smaller value of dv/dt than a clearer bottle. Thus for a dense portion of the bottle a lower reference threshold should be used for the comparison and this is achieved by making the threshold level vary in the same sense as the average transmission. It should also be noted that the circuit of FIG. 7 includes a high frequency filter 63 following the differentiating circuit 26. The function of the filter 63 is to remove high frequency noise from the differentiated signal, such noise arising both from the electrical components of the system and from minute variations in the container surface. If not removed, this noise could lead to spurious fault-indicating signals at the comparator 27.

As mentioned earlier, where the circuit of FIG. 7 is used both for initially generating the contents of the RAM 42 as well as for the subsequent container inspection, it is advantageous to set the reference threshold, as determined by the potentiometer 62, at a lower level during the learning mode of the system than during the subsequent test mode to accommodate undulations in the internal surface of the container.

The embodiments described above use three laser beams for scanning the container. However, as mentioned above, it is possible to use two beams only, such as the beams B1 and B3, directed respectively at an acute angle and an obtuse angle to the forward direction of motion of the container. In such case the two beams are preferably disposed normal to one another and make angles $\theta_1 = 135°$ and $\theta_3 = 45°$ with the forward direction of the containers. In such case, of course, only two light collectors L1 and L3 are used together with their associated signal processing circuitry, and as pointed out above it is preferred when only two beams are used to arrange that the counter 59 counts the overall number of valid fault-indicating signals originating in respect of both light collectors, and provides a reject signal only when this combined total exceeds a certain limit for any container.

It is to be understood that although the third embodiment above uses a random access memory matrix for the storage of binary information defining the fault-invalid regions of the container, it is envisaged that other kinds of storage means for binary information may be used.

We claim:

1. An apparatus for the inspection of translucent containers, the apparatus comprising:
   means for transporting successive containers continuously and non-rotatably through an inspection zone;
   means for directing a plurality of light beams sideways at each container during its movement through the zone, each light beam being directed at the side of the container from a different direction relative to the container;
   deflecting means for causing each of the beams to repeatedly scan the side of the container in a direction transverse to the direction of motion of the container as the container moves fully through each beam;
   a respective opto-electronic light collector for each beam for providing a signal representing the amount of light falling thereon from the respective beam after transmission through the container;
   signal processing circuitry associated with each light collector and adapted to examine the signal therefrom according to a predetermined criterion to generate a fault-indicating signal when such criterion is fulfilled;
   means allocating to each beam a respective area of the container sidewall for which any such falt-indicating signal can be regarded as resulting from an actual fault rather than from a characteristic of an acceptable container, said area allocating means for each beam comprising a respective storage means having stored therein binary information identifying those regions (referred to herein as fault-invalid regions) of an acceptable container, as viewed in the direction of the beam, from which fault-indicating signals may be generated according to the said criterion, the contents of the storage means being the cumulative result of previously scanning a large number of containers which have been determined to be acceptable and storing each fault-indicating signal so generated as a significant bit in the storage means at an address corresponding to the position of the beam relative to the container; and
   suppression means responsive to the stored binary information to suppress any falt-indicating signal generated while scanning a fault-invalid region of the container.

2. An apparatus according to claim 1 wherein the area of the container sidewall allocated to each beam is rectilinear and is defined at least in part by the duration of a gating signal.

3. An apparatus according to claim 1, wherein the suppression means comprises means for reading out the contents of the storage means in synchronism with the scanning of the container, and blanking any fault-indicating signal which occurs simultaneously with an output of the storage means which identifies the point currently being scanned by the beam as lying within a fault-invalid region of the container.

4. An apparatus according to claim 1, wherein the suppression means comprises means for storing the fault-indicating signals generated during the scanning in a further storage means, subsequently reading out and comparing the contents of the first and further storage means, and blanking any fault-indicating signal which occurs as output from the further storage means when the corresponding output from the first storage means indicates a fault-invalid region of the container.

5. An apparatus according to claim 1, or 4 wherein the signal processing circuitry associated with each light collector is adapted to differentiate the signal therefrom so as to provide a further signal representing the rate of change of amplitude of the light collector signal, and to compare the further signal with a reference threshold level so as to generate a fault-indicating signal when the rate of change of amplitude exceeds the threshold level.

6. An apparatus according to claim 5, wherein the said signal processing circuitry is the same as that previously used in the operation of accummulating information in the storage means but has a higher reference threshold level.

7. An apparatus according to claim 6, wherein the reference threshold level at any point in the scanning is a function of the average transmission through the container at that point, and varies in the same sense as the average transmission.

8. An apparatus according to claim 1, wherein three light beams are used and means are provided for individually summing the number of unsuppressed fault-indicating signals in respect of each associated light collector and providing a container reject signal when the total in respect of any one light collector exceeds a certain limit.

9. An apparatus according to claim 1, wherein two light beams are used and means are provided for summing the overall number of unsuppressed fault-indicating signals in respect of both associated light collectors and providing a container reject signal when the overall total in respect of the light collectors exceeds a certain limit.

10. An apparatus according to claim 1 wherein the storage means comprises a random access memory.

11. An apparatus for the inspection of translucent containers, the apparatus comprising:
   means for transporting successive containers through an inspection zone;
   means for directing at least one light beam sideways at each container in the inspection zone;
   deflecting means for causing the light beam to repeatedly scan the side of the container in a direction transverse to the direction of motion of the container in the inspection zone;

an opto-electronic light collector for providing a signal representing the amount of light falling thereon from the light beam after transmission through the container;

signal processing circuitry associated with the light collector and adapted to examine the signal therefrom according to a predetermined criterion to generate a fault-indicating signal when such criterion is fulfilled;

means allocating to the light beam a respective area of the container sidewall for which any such fault-indicating signal can be regarded as resulting from an actual fault rather than from a characteristic of an acceptable container, said area allocating means comprising a storage means having stored therein binary information identifying those regions (referred to herein as fault-invalid regions) of an acceptable container, as viewed in the direction of the beam, from which fault-indicating signals may be generated according to the said criterion, the contents of the storage means being the cumulative result of previously scanning a large number of containers which have been determined to be acceptable and storing each fault-indicating signal so generated as a significant bit in the storage means at an address corresponding to the position of the beam relative to the container; and suppression means responsive to the stored binary information to suppress any fault-indicating signal generated while scanning a fault-invalid region of the container.

* * * * *